{| style="width:100%"
|}

United States Patent [19]

Fülberth et al.

[11] Patent Number: 4,859,471

[45] Date of Patent: Aug. 22, 1989

[54] PANCREATIC ENZYME PRODUCTS AND A PROCESS FOR THE PREPARATION THEREOF

[76] Inventors: Werner Fülberth; Hans-Georg Freuer, both of Hoechst Aktiengesellschaft, P.O. Box 80 03 20, D-6230 Frankfurt am Main 80, Fed. Rep. of Germany

[21] Appl. No.: 170,562

[22] Filed: Mar. 14, 1988

Related U.S. Application Data

[63] Continuation of Ser. No. 807,490, Dec. 10, 1985, abandoned.

[30] Foreign Application Priority Data

Dec. 12, 1984 [DE] Fed. Rep. of Germany ....... 3445301

[51] Int. Cl.⁴ .................. A61K 9/22; A61K 9/34; A61K 37/62
[52] U.S. Cl. .................... 424/480; 424/481; 424/94.21
[58] Field of Search ............ 424/94.21, 480, 481

[56] References Cited

FOREIGN PATENT DOCUMENTS 1063758  8/1959  Fed. Rep. of Germany .
2035739  1/1972  Fed. Rep. of Germany .
1537651  9/1968  France .
163891   9/1933  Switzerland .
986254   3/1965  United Kingdom .

OTHER PUBLICATIONS

Remington's Phar. Sci. 15th Ed. 1975, pp. 1612–1616.
Graf et al., Pharm. Ind., vol. 45: 265, 1983.
Derwent Ref. No. 08153T–B (1972).
"Pharmazeutische Verfugbarkeit von Pankreatin-Fertigarzneimitteln" by Moller, Pharmazeutische Zeitung, vol. 125, p. 2254 (1980).
Studies on the Direct Compression of Pharmaceuticals, Graf et al., Pharm Ind., vol. 44, p. 317 (1982).
Studies on the Direct Compression of Pharmaceuticals, Graf et al., Pharm. Ind., vol. 45, p. 295 (1983).
Translation of claim 1 of French Patent No. 1,537,651, German Patent Application No. 1,063,758, Swiss Patent No. 163,891.

Primary Examiner—John W. Rollins

[57] ABSTRACT

A process for the preparation of pancreatic enzyme products in compressed form is described. A water-based insulating layer and a final lacquer based on organic solvents are applied to the core which contains the active compounds.

7 Claims, No Drawings

PANCREATIC ENZYME PRODUCTS AND A PROCESS FOR THE PREPARATION THEREOF

This application is a continuation of application Ser. No. 807,490, filed Dec. 10, 1985, now abandoned.

The following are the requirements made of pancreatic enzyme products which are used for the treatment of digestive insufficiency:

They should contain an adequate quantity of pancreatic enzyme of good quality. This presupposes high enzyme activity. However, the therapeutic value of these products is only ensured when their pharmaceutical processing is appropriate for the high enzyme activity. An important prerequisite for effective replacement treatment is, amongst others, rapid and complete release of the enzymes in the digestive tract. Under the pH conditions of the duodenum the formulations ought to release the enzymes having digestive activity immediately. Thus, the essential criteria of quality of pancreatic enzyme formulations emerge as being the initial activity of the enzymes, resistance to gastric juice to protect against the inactivating effect of gastric acid, and the disintegration time and release rate of the enzymes, particular importance being attached to lipase release for effective pancreatic enzyme replacement. Another requirement relates to the stability of the enzymes throughout the preparation process and during storage.

In the preparation of pancreatic enzyme products, especially when they contain a high percentage of organic dry enzyme products, it is necessary to overcome substance-specific and processing technological difficulties which are an obstacle to the requirements made of this product group. Thus, there have already been descriptions of the necessary enzymes from a large number of commercial products not being released in a sufficient quantity, and especially not at the suitable time (H. Möller, Pharm. Ztg. 125, 2254–2258 (1980)). In addition, preparation- and storage-related enzyme losses have been found in comparative testing. However, it is also noticeable that many products, especially those with a high enzyme content, do not meet pharmacopeia requirements for tablets which have coatings soluble in gastric juice or enteric coatings.

Although pancreatin products can still, at a moderate dose of 300–400 mg, be formulated to comply with the biopharmaceutical demands, nevertheless problems become evident when the intention is to convert quantities of 700–800 mg of pancreatin into a drug form suitable for patients, since the release rate of the high-dosed products, in particular, is very low compared with the lower-dosed. For this reason, there are indications in the literaure only for the preparation of compressed, rapidly disintegrating pancreatin formulations containing a moderate dose of 300–400 mg (cf. for example, German Offenlegungsschrift 2,035,739 or the corresponding Derwent Ref. 08513 T (1972)).

No directive for the preparation of high-dosed, single-dose drug forms with rapid release has been described to date.

Since the release rate of the enzymes and the disintegration characteristics of compressed pancreatic enzyme products are directly related, it is indispensable to use a highly active tablet disintegrant for the high-dosed products having a pancreatin content of 700–800 mg. The use of tablet disintegrants for pancreatic enzyme products has already been described (cf. E. Graf et. al. Pharm. Ind. 44, 317–321 (1982)).

The difficulty with the preparation of high-dosed pancreatin products comprises the provision of a protective coating based on organic solvents on the pancreatin core which, for rapid enzyme release, ought to contain a high proportion of a highly active tablet disintegrant. The protective coatings are necessary to counteract the inactivatng effect of gastric juice and to reduce environmental effects which diminish stability. In addition, they prevent undesired contact with the pancreatic enzyme during the swallowing process. According to the state of the art, they are applied as lacquers based on organic solvents. Solvents which have proved to be especially innocuous to enzymes are chloroform, acetone and isopropanol. Water, especially in conjunction with heat, should be avoided because of its enzyme-inactivating effect (cf. E. Graf et al., Pharm. Ind. 45, 295–299 (1983)). Solvent penetrates into the cores during the lacquering process. When disintegrants are present, the cores swell up and are mechanically crushed during the lacquering process. Although cores containing no disintegrant, as in the case of the low-dosed products, can be lacquered the unavoidable residual solvent remaining in the core (even in traces) brings about physical changes in the film during storage.

The problem now is to avoid the penetration of solvents into the film-coated tablet cores during the lacquering process. Not the least of the reasons why this is necessary is because small quantities of residual solvent remaining in the core generate a swelling pressure by acting on the tablet disintegrant even after storage, especially at elevated temperatures. The result is then the formation of hairline-cracks and changes in the pore structure in the protective film.

An additional factor diminishing stability results from the interaction between the pancreatin and the film covering. In the case of film-forming agents containing ester groups, during storage the lipase contained in pancreatin may lead to ester cleavage and thus to a chemical change in the film, which adversely affects the resistance to gastric juice.

It has now been found, surprisingly, that the penetration of solvents into pancreatin cores, and thus also direct contact between the core and the protective film which has been sprayed on from a solvent, can be avoided by first providing the pancreatin cores with a water-based insulating layer.

Thus the invention relates to a process for the preparation of a pancreatic enzyme product in compressed form, which comprises application to the core, which contains the active compound, of a water-based insulating layer which is composed of a primary covering syrup and a primary covering powder, and then provision of a lacquer layer based on organic solvents, and to products obtainable by this process.

It was not predictable that specifically an insulating layer applied with water would be able effectively to protect the pancreatin core, since it is known that water, specifically, has an enzyme-inactivating effect, especially under the influence of heat.

The insulating layer is applied in two phases in the process according to the invention. In the first phase, a primary covering syrup, which is preferably warmed, is added to the cores until they begin to adhere. Subsequently, primary covering powder is added until the cores roll freely again. Before the application of the next primary layer the cores with their primary cover must be thoroughly dried. This can be carried out with an airblower. In general, two to five of these primary covering layers suffice for effective protection against penetrating solvent and for the insulation of the core against the final film layer. The final film layer is a lacquer layer based on organic solvents. It can be soluble in gastric juice or enteric.

Both low-dosed pancreatic enzyme products, which are those having an active compound content up to about 500 mg, and high-dosed products, those containing about 500–1000 mg of pancreatic enzymes, are obtained by the process according to the invention.

Tablet disintegrants are not absolutely necessary for low-dosed pancreatic enzyme products. Thus, the preparation problems associated with the presence of highly active tablet disintegrants are avoided to a large extent. However, it has emerged that, owing to the separation of the core from the final lacquer, the storage-related change in the final lacquer owing to the effect of residual solvents in the core does not take place, and the storage-related loss of resistance to gastric juice can be avoided.

In contrast, the addition of a tablet disintegrant is necessary in the preparation of high-dosed products.

The high-dosed pancreatin cores containing a large amount of an active table disintegrant are effectively protected, by water-based primary covering layers, against the penetration of solvents during the final lacquering process without this entailing any change in their enzyme-release characteristics.

The cores acquire adequate mechanical stabilization by the primary covering layer, so that no abrasion due to rolling during the lacquering process is detectable.

The formulations according to the invention contain, for example, 100 to 1000 mg, preferably 500 to 1000 mg, in particular 700 to 800 mg, of pancreatin per dosage unit. They can contain in the core other active compounds customary for pancreatic enzyme products, such as dimethylpolysiloxane, ox bile, dehydrocholic acid, hemicellulase, bromelain, plant lipase concentrates and 2-ethoxy-6,9-diaminoacridine D,L-lactate (or other physiologically tolerated salts thereof).

Suitable tablet disintegrants which accelerate disintegration and release are the following disintegrants, in a concentration of 1 to 20% by weight (preferably 5 to 15%) based on the content of pancreatin: crosslinked sodium carboxymethylcellulose, low-substituted hydroxypropylcellulose, sodium carboxymethylstarch, formaldehyde/casein, crosslinked polyvinylpyrrolidone, calcium carboxymethylcellulose and sodium amylopectin glycolate. To support the disintegration-accelerating action of the abovementioned disintegrating auxiliaries, it is possible to add, for example, sodium chloride.

Examples of other suitable auxiliaries and vehicles are microcrystalline cellulose, polyethylene glycol, powdered fibrous cellulose, highly disperse silica, dicalcium phosphate dihydrate and aluminum hydroxide gel.

So-called insulating or primary covering layers are applied for the insulation of the core containing pancreatin. These primary covering layers, which are applied in 2 phases, are composed of a primary covering syrup, for example an aqueous sugar syrup, 50 to 65%, with minor additives, such as gelatine, gum arabic, starch, polyvinylpyrrolidone, highly disperse silica, sodium carboxymethylcellulose, sodium alginate, polyvinyl alcohol or calcium carbonate. They are furthermore composed of a primary covering powder. Mixtures containing talc, calcium carbonate, powdered sucrose, highly disperse silica, titanium dioxide or gum arabic are preferably used for this. The final film layer can be either soluble in gastric juice or resistant to gastric juice.

The lacquers which are soluble in gastric juice contain the following film-forming agents, for example: hydroxypropylcellulose, hydroxypropylmethylcellulose, hydroxyethylcellulose, and a copolymer which has cationic properties and is based on dimethylaminoethyl methacrylate and neutral methacrylic ester (Eudragit ®—E).

The protective casings which are resistant to gastric juice are composed of, for example, cellulose acetate phthalate, hydroxypropylmethylcellulose phthalate, polyvinyl acetate phthalate, and copolymers which have anionic properties and are based on methacrylic acid and methacrylic esters (Eudragit ® L or S). Auxiliaries, such as titanium dioxide, iron oxide pigments, talc and plasticizers, such as polyethylene glycols, castor oil, triethyl citrate, phthalic esters and glycerol fatty acid esters, are also suitable for both lacquer systems. Customary organic solvents, where appropriate mixed with water, are used for both lacquer systems.

The products obtained by the process according to the invention, including the high-dosed products, are very mechanically stable. The mechanical protection was evident even after storage at +40° C. Pancreatin enteric film-coated tablets prepared according to the invention showed no external changes even after 6 months (+40° C.). No hairline-cracks were evident on the lacquer surface, and the test for resistance to gastric juice complied with the requirements of the European Pharmacopoeia.

The release of lipase from a pancreatic enzyme product is a parameter for testing the pharmaceutical availability of pancreatin. It was determined as described below for high-dosed products according to the invention and known products.

The known products I, II, III and IV had the following compositions:

| I: | Pancreatin | 700 g | |
| | purified, dried ox | | |
| | bile | 50 mg | film-coated tablets |
| | auxiliaries | 345 mg | |
| II: | Pancreatin | 700 mg | |
| | total bile | 50 mg | |
| | acids (fel suis) | | |
| | (calculated as cholic | | |
| | acid) | | film-coated tablets |
| | auxiliaries | 60 mg | |
| III: | Pancreatin | 800 mg | |
| | auxiliaries | 92 mg | film-coated tablets |
| IV: | Pancreatin | 700 mg | |
| | dried extract from | 120 mg | |
| | *Aspergillus oryzae* | | film-coated tablets |
| | auxiliaries | 650 mg | |

Of the products prepared according to the invention, those of Examples 1 and 3 were investigated.

The test of the release of lipase was carried out by method II described by H. Möller (Pharm. Ztg. 125, 2254–2258 (1980)):

USP XX paddle apparatus
Test liquid
NaCl 2.0 g
$NaH_2PO_4H_2O$ 9.2 g
distilled water ad 1000 ml The test liquid was adjusted, as required, to pH 3 or pH 6 with 6N HCl or concentrated NaOH respectively.

| | | |
|---|---|---|
| Test liquid pH 3 | 0.75 | hour |
| Test liquid pH 6 | 2.25 | hours |
| 600 ml of test liquid, 37° C., | 100 | rpm. |

The results of the tests are compiled in the table below. Comparative evaluation of the release of lipase by the method of H. Möller, as a parameter for testing the pharmaceutical availability of pancreatin

| Product | I | II | III | IV | Corresponding to Example 1 | Corresponding to Example 3 |
|---|---|---|---|---|---|---|
| Lipase activity determined in FIP units | 24,364 | 26,599 | 30,006 | 26,806 | 6,568 | 36,171 |
| % lipase activity released after | | | | | | |
| 45 minutes | 2 | 2 | 1 | 1.5 | 6 | 1.3 |
| 75 minutes | 2 | 2 | 2 | 3.5 | 6 | 8.5 |
| 130 minutes | 3 | 3 | 2 | 63.2 | 63 | 74.1 |
| 180 minutes | 5 | 3 | 3 | 63.5 | 100 | 96.7 |

As can be seen from the results the enzyme lipase which is important for the digestive process is not released in sufficient concentration and, in particular, is not released at a suitable time with the products tested for comparison. The formulations prepared according to the invention completely, or virtually completely, release the indicator enzyme lipase in the period essential for the digestive process, ie. within 2 hours after passage through the stomcah.

A prerequisite for the acceleration of the enzyme release, especially with products containing a high dose of pancreatin, is the use of highly active tablet disintegrants which in turn can only fulfil their purpose if the pancreatin core has been insulated with a water-based protective layer according to the invention before the final lacquering.

The examples which follow are intended to illustrate the invention:

EXAMPLE 1

Preparation of 10,000 coated tablets:
1. For the preparation of the tablet cores
1. 2.10 kg of pancreatin
2. 0.50 kg of hemicellulase
3. 0.25 kg of ox bile, dried and
4. 0.15 kg of sodium chloride are mixed and processed, by compression in a tablet press or roller mill followed by comminution, to give granules of particle size about 1.5 mm.
   3.0 kg of the granules thus prepared (1. to 4.) are compressed to give cores with a final weight of 300 mg.
2. For the preparation of the primary covering syrup

| | |
|---|---|
| 10.00 kg | of sugar are dissolved, with heating, in |
| 2.50 kg | of demineralized water |
| 12.50 kg | = sugar solution A, and |
| 0.50 kg | of gelatine are dissolved, with heating, in |
| 2.50 kg | of demineralized water |
| 3.00 kg | = gelatine solution B, and |
| 12.50 kg | of sugar solution A, |
| 3.00 kg | of gelatine solution B, and |
| 3.75 kg | of starch syrup which has previously been liquified on a water bath, are mixed |
| 19.25 kg. | |

3. For the preparation of the primary covering powder, equal parts of talc and calcium carbonate are mixed.

The cores are provided with 3 primary covering layers (insulating layers) in a coating vessel in the following manner:

First the warmed primary covering syrup 2. is added to the cores, which are in motion in the vessel, until they start to adhere.

Then primary covering powder 3. is added until the cores roll freely again. This process is repeated 3 times with interpolation of drying periods.

The dried cores are provided in the customary manner with an enteric protective lacquer and are then coated.

EXAMPLE 2

Preparation of 10,000 film-coated tablets
1. 5.00 kg of pancreatin,
2. 0.35 kg of microcrystalline cellulose, and
3. 0.40 kg of sodium chloride are mixed and processed, by compaction in a tablet press or roller mill and subsequent comminution, to give granules of particle size about 1.5 mm.
   5.75 kg of the granules thus prepared are mixed in a suitable mixer with
4. 0.50 kg of crosslinked polyvinylpyrrolidone, and
5. 0.05 kg of highly disperse silica.
   6.30 kg of the granules (1. to 5.) are compressed to form tablets with a final weight of 630 mg and are provided with 3 primary covering layers in the manner described in Example 1 and are then, depending on requirements, provided with a protective lacquer which is soluble in gastric juice or is enteric.

EXAMPLE 3

Preparation of 10,000 film-coated tablets:
1. 8.00 kg of pancreatin and
2. 0.65 kg of sodium chloride are mixed.
   8.65 kg of this mixture (1.-2.) are compacted and processed by subsequent comminution to give granules of particle size about 1.5 mm.
   8.65 kg of granules (1.-2.) are mixed with
3. 0.55 kg of microcrystalline cellulose and
4. 0.80 kg of crosslinked polyvinylpyrrolidone.
   10.00 kg of the granules (1.-4.) are compressed to form cores with a final weight of 1,000 mg and are provided with 3 primary covering layers in the manner described in Example 1.

After drying, depending on requirements, a protective lacquer which is soluble in gastric juice or is enteric is applied.

EXAMPLE 4

Preparation of 10,000 film-coated tablets:
1. 2.10 kg of pancreatin and
2. 0.49 kg of microcrystalline cellulose are mixed and processed, by compaction followed by comminution, to give granules of particle size about 1.5 mm (granules A).
3. 0.80 kg of dimethylpolysiloxane and
4. 0.80 kg of highly disperse silica, hydrophobic, are mixed.
   1.60 kg of this mixture (3.–4.) and
5. 0.80 kg of microcrystalline cellulose are mixed.
   2.40 kg of the mixture (3.–5.) are compacted and processed by comminution to give granules of particle size about 1.5 mm (granules B).
   2.59 kg of granules A (1.–2.),
   2.40 kg of granules B (3.–5.),
6. 0.08 kg of microcrystalline cellulose,
7. 0.30 kg of crosslinked polyvinylpyrrolidone,
8. 0.10 kg of highly disperse silica, and
9. 0.03 kg of magnesium stearate are mixed.
   5.5 kg of these mixed granules are compressed to form cores with a final weight of 550 mg and are provided with 3 primary covering layers in the manner described in Example 1.
   The cores with their primary cover are coated in the customary manner with a final enteric lacquer.

EXAMPLE 5

Preparation of 10,000 film-coated tablets:
1. 4.20 kg of granulated pancreatin,
2. 0.50 kg of dried ox bile,
3. 1.00 kg of hemicellulase,
4. 0.30 kg of sodium chloride,
5. 0.30 kg of crosslinked sodium carboxymethylcellulose,
6. 0.17 kg of talc, and
7. 0.03 kg of highly disperse silica are mixed and compressed to form cores with a final weight of 650 mg. The cores are provided with 3 primary covering layers in the manner described in Example 1 and are then coated with an enteric protective lacquer.

EXAMPLE 6

Preparation of 10,000 film-coated tablets:
1. 7.00 kg of pancreatin,
2. 0.05 kg of highly disperse silica, and
3. 0.60 kg of sodium chloride are mixed.
   7.65 kg of this mixture (1.–3.) are compacted and processed by subsequent comminution to give granules of particle size about 1.5 mm.
   7.65 kg of granules (1.–3.) are mixed with
4. 0.80 kg of microcrystalline cellulose,
5. 0.05 kg of highly disperse silica, and
6. 1.00 kg of crosslinked sodium carboxymethylcellulose.
   9.50 kg of the granules (1.–6.) are compressed to form cores with a final weight of 950 mg and are provided with 3 primary covering layers in the manner described in Example 1.
   After drying, a protective coating which is soluble in gastric juice and is based on organic solvents is applied.

We claim:

1. A process for the preparation of a high-dosage pancreatic enzyme product in compressed form, which comprises application to the core, which contains the active compound, of a water-based insulating layer which is composed of a primary covering syrup and a primary covering powder, and then provision of a lacquer layer based on an organic solvent.

2. The process as claimed in claim 1, wherein sugar syrup, which can also contain gelatine and starch, is used as the primary covering syrup.

3. The process as claimed in claim 1, wherein a mixture of talc and calcium carbonate is used as the primary covering powder.

4. A pancreatic enzyme product obtainable by the process as claimed in claim 1.

5. A pancreatic enzyme product obtainable by the process as claimed in claim 1, which contains in the core 500 to 1,000 mg of pancreatic enzyme and 1 to 20% by weight, relative to pancreatic enzyme, of a customary disintegrant.

6. A pancreatic enzyme product obtainable by the process as claimed in claim 1, which contains in the core 700 to 800 mg of pancreatic enzyme and 1 to 20% by weight, relative to pancreatic enzyme, of a customary disintegrant.

7. A pancreatic enzyme product obtainable by the process as claimed in claim 1, which also contains in the core other active compounds customary for pancreatic enzyme products.

* * * * *

UNITED STATES PATENT AND TRADEMARK OFFICE
CERTIFICATE OF CORRECTION

PATENT NO. : 4,859,471

DATED : August 22, 1989

INVENTOR(S) : WERNER FÜLBERTH ET AL.

It is certified that error appears in the above-identified patent and that said Letters Patent is hereby corrected as shown below:   Title page:

Item [76] The inventors' residence addresses should read as follows:

Inventors:  WERNER FULBERTH, Kelkheim; and
HANS-GEORG FREUER, Frankfurt am Main; both of the Federal Republic of Germany; and Item [76] The assignee should be identified as follows:

Assignee:  HOECHST AKTIENGESELLSCHAFT
Frankfurt am Main, Federal Republic of Germany Signed and Sealed this Third Day of April, 1990

Attest:

HARRY F. MANBECK, JR.

*Attesting Officer*   *Commissioner of Patents and Trademarks*